(12) United States Patent
Lee et al.

(10) Patent No.: US 6,247,349 B1
(45) Date of Patent: *Jun. 19, 2001

(54) POLYMER-BASED HUMIDITY SENSING ELEMENTS

(75) Inventors: Chun-Yuan Lee, Chiang-Fu Hsien; Ping Ping Tsai, Chutung; Chia-Jung Lu, Taipei, all of (TW)

(73) Assignee: Industrial Technology Research Institute, Hsinch Hsien (TW)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/801,886

(22) Filed: Feb. 18, 1997

(51) Int. Cl.$^7$ ........................................ G01N 9/36
(52) U.S. Cl. ........................... 73/29.05; 73/335.05
(58) Field of Search ...................... 73/29.05, 335.03, 73/335.04

(56) References Cited

U.S. PATENT DOCUMENTS

| | | | |
|---|---|---|---|
| 4,529,642 | * 7/1985 | Miyoshi et al. | 428/201 |
| 5,356,936 | * 10/1994 | Howell et al. | 521/27 |

FOREIGN PATENT DOCUMENTS

| | | | | |
|---|---|---|---|---|
| 86447 | * | 5/1983 | (JP) | 73/29.05 |
| 2210253 | * | 8/1990 | (JP) | 73/29.05 |
| 4309855 | * | 11/1992 | (JP) | 73/29.05 |

* cited by examiner

Primary Examiner—Hezron Williams
Assistant Examiner—Willie Morris Worth
(74) Attorney, Agent, or Firm—W. Wayne Liauh

(57) ABSTRACT

A porous poly(2-acryl-amido-2-methyl-propane sulphonic acid)-based humidity sensing element is disclosed which provides improved range of humidity measurement and response time with little or no hysteresis. It includes: (a) a non-conductive substrate which has a pair of electrodes formed thereon; (b) a porous poly(2-acryl-amido-2-methyl-propane sulphonic acid) film formed on said electrodes. The porous poly(2-acryl-amido-2-methyl-propane sulphonic acid) film is formed by first forming a non-porous poly(2-acryl-amido-2-methyl-propane sulphonic acid) film on the electrodes, then subjecting the non-porous poly(2-acryl-amido-2-methyl-propane sulphonic acid) film to a heat treatment at temperatures between about 170° C. and 240° C. such that a porous structure is formed in said poly(2-acryl-amido-2-methyl-propane sulphonic acid) film. The poly(2-acryl-amido-2-methyl-propane sulphonic acid) can be modified by incorporating a cation, such as hydrogen, lithium, potassium, sodium, ammonium, primary, secondary, and tertiary amine ions, and tetra-alkyl ammonium ions.

17 Claims, 3 Drawing Sheets

POLYMER-BASED HUMIDITY SENSING ELEMENTS

FIELD OF THE INVENTION

The present invention relates to an improved polymer-based humidity sensing element. More specifically, the present invention relates to a poly(2-acrylamido-2-methylpropanesulfonic acid)-based impedance-type humidity sensor with improved response time and reduced hysteresis, and the novel method of making the same.

BACKGROUND OF THE INVENTION

Humidity sensors based on electric signals have become very popular in recent times. A humidity sensor measures the humidity content in the surrounding environment. More recently, polymeric films have been used as a humidity sensing element. Polymer-based humidity sensing elements can generally be classified into two categories: capacitance-type and impedance-type. The former typically involves more complicated circuit design and manufacturing process, and thus is more expensive, than the latter. A impedance-type electric humidity sensing element changes its electrical impedance as the humidity of the surrounding environment changes, and the measured impedance is converted into humidity readings.

The polymer-based sensing elements can also be further classified into two categories: porous (or more specifically, micro-porous) type, and non-porous type. There are numerous examples of porous polymer film based impedance-type humidity sensors. One of the examples is a microporous polyethylene film, in which 2-acrylamido-2-methylpropane sulfonic acid was graft-polymerized by ultraviolet irradiation. There are also numerous examples of non-porous polymer film based humidity sensors. One of the examples is a three-polymer-coated quartz crystal whose frequency varies as a function of the change in humidity. The first example is discussed in an article entitled: "Humidity Sensor Composed of a Microporous Film of Polyethylene-Grafted-Poly-(2-Acrylamido-2-Methylpropane Sulfonate)," by Y. Sakai, et al., *Polymer Bulletin*, 18, 501–506 (1987). The second example is discussed in another article entitled: "Relative Humidity Measurements Using A Coated Piezoelectric Quartz Crystal Sensor," *Sensors and Actuators*, 11 319–328 (1987). The three polymer coatings used in the second example include HEM-AMPS copolymer (HEM=2-hydroxyethyhnethyacrylate, AMPS=2-acryl-amido-2-methyl-propane sulphonic acid); cellulose acetate; and a modified epoxy resin. When moisture is absorbed by the polymer coating, the mass of the crystal is changed, causing its oscillating frequency to be changed.

The above two examples are specifically mentioned here because they both involve the use of PAMPS (poly(2-acryl-amido-2-methyl-propane sulphonic acid)) in the sensing element. In these examples, PAMPS itself is non-porous (as in Example 2). To make a porous polymer film, the PAMPS must be graft-polymerized into a micro-pourous polyethlene film. This unavoidably complicates the manufacturing process and increases the production cost.

Non-porous PAMPS can be used in making a impedance-type electric humidity sensing element by forming a PAMPS film on a pair of electrodes. However, the thickness of the non-porous PAMPS film must be carefully controlled within a very narrow range. If the PAMPS film is too thick, several undesirable effects, such as slow response time and significant hysteresis, will be experienced. On the other hand, if the PAMPS film is too thin, the impedance will be too high. Porous polymer-based sensing elements can provide the advantages of quick response time and small hysteresis. However, these advantages, at the present time, cannot be enjoyed by PAMPS-based sensing elements, without the extra step of grafting the PAMPS polymer into another polymer, such as polyethylene.

SUMMARY OF THE INVENTION

The primary object of the present invention is to develop a impedance-type PAMPS-based (poly(2-acryl-amido-2-methyl-propane sulphonic acid)) electric humidity sensor with quick response time and low hysteresis. More specifically, the primary object of the present invention is to develop a method, according to which porous impedance-type PAMPS-based electric humidity sensors can be prepared which possess quick response time and low hysteresis. In the past, PAMPS can only be provided in the form of a non-porous film, which typically exhibits slow response time and undesirable hysteresis effects when used as a humidity sensing element. Moreover, the conventional non-porous PAMPS films are not very stable in high humidity environment; they typically become water-soluble when the humidity exceeds about 70% RH. With the present invention, the porosity of the novel porous PAMPS films allows the water molecules to travel in and out more speedily. The novel porous PAMPS-based humidity sensing elements of the present invention also exhibit substantially improved stability over the conventional elements; they maintain excellent stability at humidities as high as 95% RH without any observable hysteresis and the response time is well within 1–2 minutes.

In the present invention, the humidity sensing element is made using a two-stage process. In the first stage, poly(2-acryl-amido-2-methyl-propane sulphonic acid) is prepared by polymerizing 2-acryl-amido-2-methyl-propane sulphonic acid in the presence of small amounts of an initiator, such as AIBN, and other desirable additives. In the second stage, a film of poly(2-acryl-amido-2-methyl-propane sulphonic acid) with a thickness of about 5–30 $\mu$m is formed on a pair of electrodes that have been formed on a insulative substrate, such as aluminum oxide, and the polymer film is heated at a temperature between about 170–240° C. The poly(2-acryl-amido-2-methyl-propane sulphonic acid)-based humidity sensing element so prepared has a porous structure when observed under a microscope; it also shows a white/light yellow or brownish surface color, and exhibits excellent stability, quick response time, and little or no hysteresis. If the heat treatment temperature is too low during the second stage (i.e., less than 170° C.), it was difficult to form a porous structure. On the other hand, if the temperature is too high (i.e., greater than 240° C.), the polymer molecules are likely to be degraded, resulting in substantially high impedance.

Poly(2-acryl-amido-2-methyl-propane sulphonic acid) is a polymeric electrolyte which can be converted into a protonic electrical conductor (in the form of a Bronsted acid) when subject to an alternating current. Preferably, aqueous solutions containing conductive ions such as lithium hydroxide, sodium hydroxide, potassium hydroxide, or ammonium hydroxide, can be added into the aqueous 2-acryl-amido-2-methyl-propane sulphonic acid solution before or during the polymerization reaction, to form a modified PAMPS, represented as PAMPS•X, wherein X is a cation, such as $H^+$, $Li^+$, $Na^+$, $K^+$, ammonium, primary to tertiary arnine ions, or tetra-alkyl ammonium ions, etc. The amount of the cations should be less than the amount of AMPS. The primary to tertiary amine ions can be methylphenylamine, trimethylamine, triethylamine, etc. The primary to tertiary amines, including ammonia, can be converted into ammonium ions by the addition of a hydrogen atom, for example, $NH_3$ will be converted into $NH_4^+$, and $HN(C_2H_4)_3$ will be converted into $HN(C_2H_4)_3^+$, etc. A higher temperature will be required to achieve the required porosity of the PAMPS film at higher ratios of amines/AMPS. However, different amines may also require different heat treatment temperatures.

BRIEF DESCRIPTION OF THE DRAWING

The present invention will be described in detail with reference to the drawing showing the preferred embodiment of the present invention, wherein.

DETAILED DESCRIPTION OF THE PREFERRED EMBODIMENT

The present discloses an impedance-type PAMPS (poly(2-acryl-amido-2-methyl-propane sulphonic acid)) -based electric humidity sensor with quick response time and low hysteresis, and the method of making the same. The PAMPS-based electric humidity sensor disclosed in the present invention has a porous structure, so as to provide a quick response time and exhibit low hysteresis. The novel porous PAMPS-based humidity sensing elements of the present invention also exhibit substantially improved stability at humidities as high as 95% RH without any observable hysteresis and the response time is well within 1–2 minutes.

Figure 1:
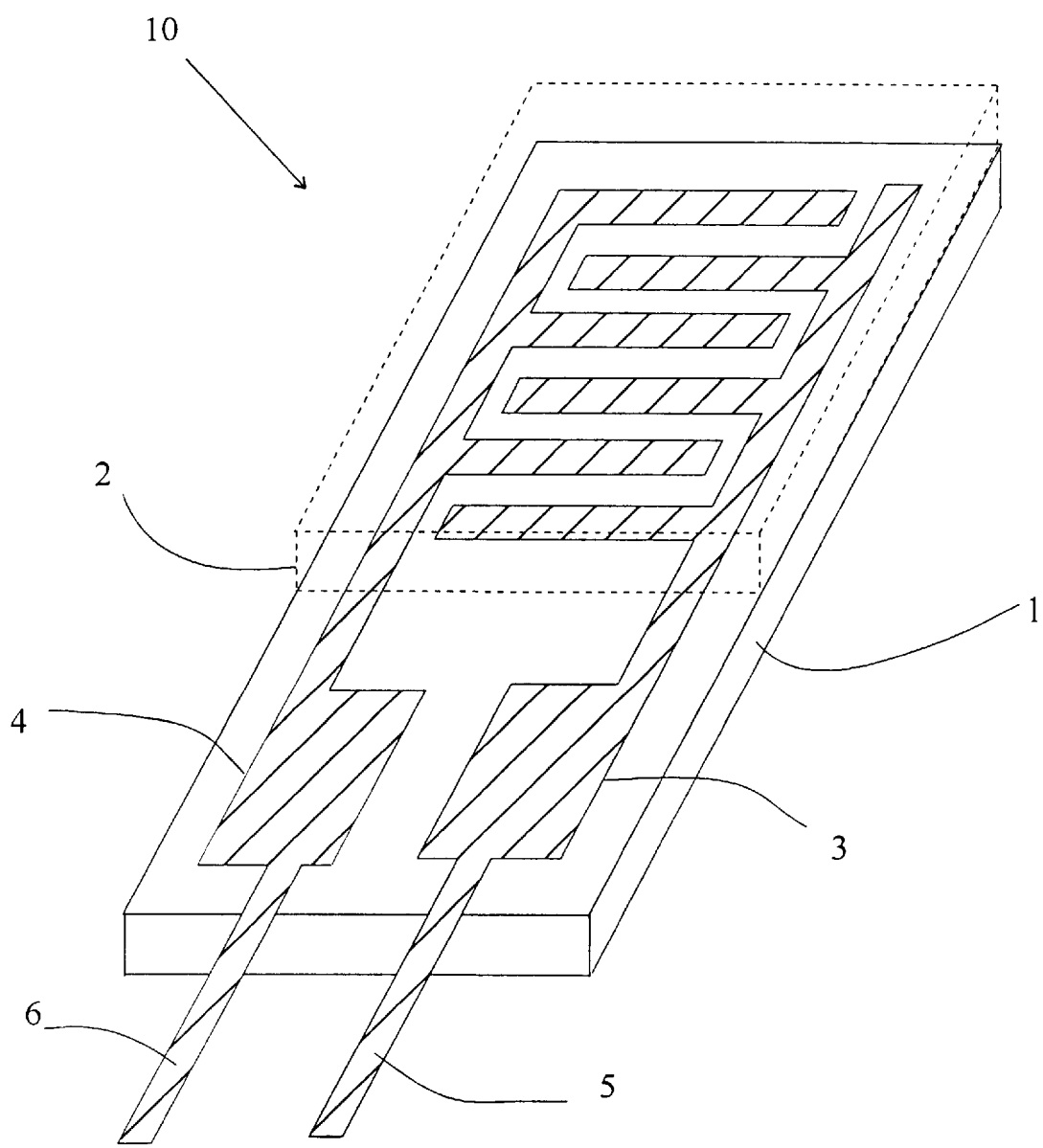
FIG. 1 is a schematic drawing showing a humidity sensing element including a substrate, a pair of electrodes, and a polymeric sensing element.

FIG. 1 is a schematic drawing showing a humidity sensing element 10, which contains a pair of electrodes, 3 and 4, formed on a substrate 1. A polymeric sensing element 2 is provided which covers both electrodes. The electrodes 3,4 can be made from silver, gold, or silver-palladium alloys. The electrodes 3 and 4 are connected to a power source and ground, respectfully, via a pair of leads, 5 and 6, respectively.

Figure 4:
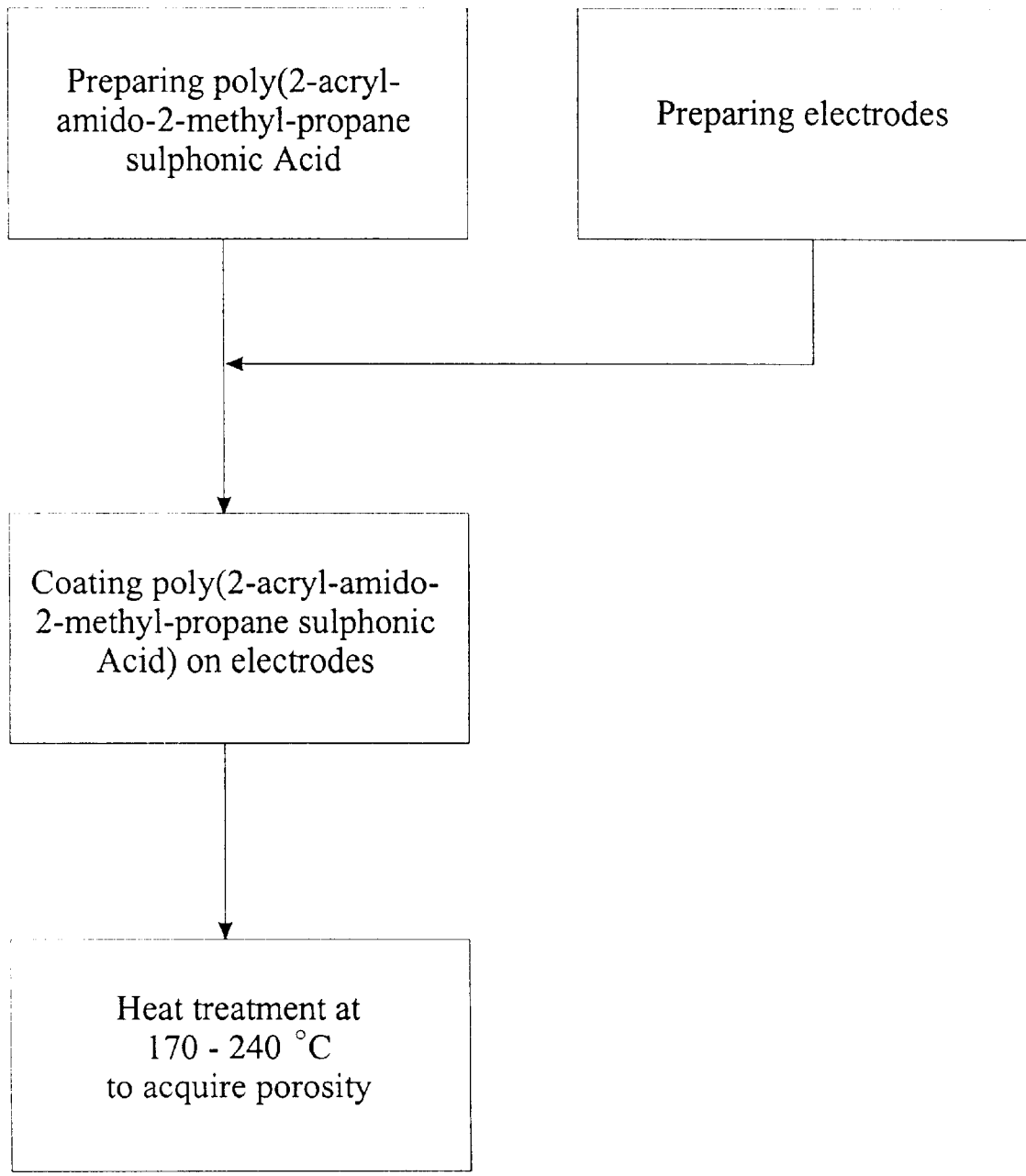
FIG. 4 is a flowchart diagram showing the key steps of the process disclosed present invention in preparing a porous poly(2-acryl-amido-2-methyl-propane sulphonic acid)-based humidity sensing element.

FIG. 4 is a flowchart diagram showing the key steps of the process disclosed present invention for preparing a porous poly(2-acryl-amido-2-methyl-propane sulphonic acid)-based humidity sensing element. The humidity sensing element was made using a two step process. First, poly(2-acryl-amido-2-methyl-propane sulphonic acid) was prepared by polymerizing 2-acryl-amido-2-methyl-propane sulphonic acid in the presence of small amounts of a polymerization initiator, such as AIBN (2,2-azobisisobutyronitrile, but many other initiators can be used), and other desirable additives. After the poly(2-acryl-amido-2-methyl-propane sulphonic acid) was made, it was coated on a pair of electrodes at a thickness of about 5–30 $\mu$m. The electrodes, which were made of silver, gold, platinum, palladium, silver-palladium alloys, ruthenium dioxide, or any other suitable electricity conductive materials, had been formed on a substrate. In the second step, the poly( 2-acryl-amido-2-methyl-propane sulphonic acid) film was heated at a temperature between about 170–240° C. to acquire a porous structure when observed under a microscope. The heat-treated poly(2-acryl-amido-2-methyl-propane sulphonic acid) showed a white/light yellow or brownish color at its surface. If the heat treatment temperature was too low (e.g., less than 170° C.), it was difficult to form a porous structure. On the other hand, if the temperature is too high (e.g., greater than 240° C.), the polymer molecules are likely to be degraded, resulting in undesirably high impedance.

Optionally, conductive cations, such as hydrogen lithium, sodium, potassium, or ammonium (including primary, secondary, or tertiary amine ions, or tetra-alkyl ammonium ions) can be added into the aqueous 2-acryl-amido-2-methyl-propane sulphonic acid solution before or during the polymerization reaction, to form a cationed-modified PAMPS, represented as PAMPS•X, wherein X is a cation, such as $H^+$, $Li^+$, $Na^+$, $K^+$, ammonium, primary to tertiary amine ions, or tetra-alkyl ammonium ions, etc. The amount of the cations should be less than the amount of AMPS. The primary to tertiary amine ions can be methylphenylamine, trimethylamine, triethylamine, etc. The primary to tertiary amines, including ammonia, can be converted into ammonium or amine ions by the addition of a hydrogen atom, for example, $NH_3$ will be converted into $NH_4^+$, and $N(C_2H_4)_3$ will be converted into $HN(C_2H_4)_3^+$, etc. Higher ratios of amines/AMPS may require higher heat-treatment temperature to provide the desired porosity of the PAMPS film. However, different types of amines may also require different heat treatment temperatures during the second step to create porosity in the polymer film.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed. In these examples, the humidity sensor contained a pair of comb-shaped electrodes which were formed from silver on a substrate. The electrodes can also be made from gold, platinum, palladium, silver-palladium alloys, ruthenium dioxide, or any other suitable electrically conductive materials.

EXAMPLE 1

Figure 2:
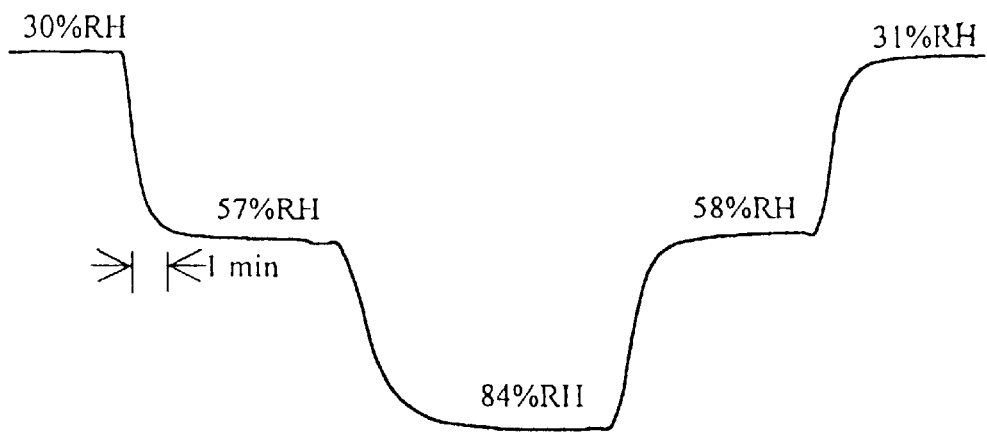
FIG. 2 is a representative response chart when the humidity sensor of the present invention is used in different environments.
Figure 3:
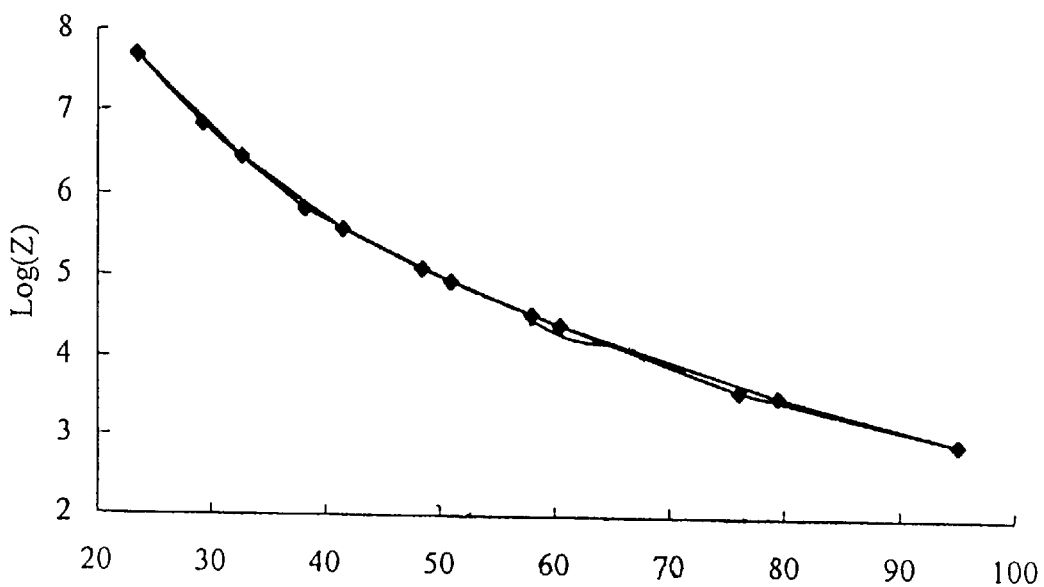
FIG. 3 is a plot of log (Z) vs. RH % measured using the humidity sensor of the present invention, indicating very low hystersis.

2 g of AMPS (2-acryl-amido-2-methyl-propane sulphonic acid) were dissolved in 5 g of water. A small amount of a polymerization initiator (AIBN) was added to the aqueous AMPS solution. After thorough mixing, the reactant mixture was heated to begin a polymerization reaction, and poly(2-acryl-amido-2-methyl-propane sulphonic acid), or PAMPS, was formed. The PAMPS was screen printed on the electrodes and then heated in a 190° C. oven for two minutes. A porous PAMPS layer was formed. The two electrodes were respectively soldered to a power source circuitry to complete the formation of a humidity sensor. FIG. 2 is a representative response chart when the humidity sensor prepared in this example was used to measure humidity. FIG. 2 shows that the response time was less than 1–2 minutes. FIG. 3 is a plot of log (Z) (impedance) vs. RH% measured using the humidity sensor prepared in this example. FIG. 3 shows that very low hystersis was observed.

EXAMPLE 2

2 g of AMPS were dissolved in 5 g of water. 0.04 g of lithium hydroxide and a small amount of a polymerization initiator were added to the aqueous AMPS solution. After thorough mixing and heating, PAMPS•Li was formed. The PAMPS•Li was screen printed onto the electrodes and then heated in a 230° C. oven to form a porous PAMPS•Li layer. In this example, the molar ratio between AMPS and LiOH was 10 to 1, and the conductive elements in the porous layer involve hydrogen and lithium ions. When the ratio of lithium ions relative to AMPS was too high, no porous structure was formed even after the PAMPS•Li layer was heat-treated at temperatures above 250° C. The lithium hydroxide can be replaced with potassium hydroxide, sodium hydroxide, or tetra-alkyl ammonium hydroxide. The ratio of cation to AMPS can be between 0 and 0.5.

EXAMPLE 3

2 g of AMPS were dissolved in 5 g of water. 0.2 g of 25% ammonia water and a small amount of a polymerization initiator were added to the aqueous AMPS solution. After thorough mixing and heating, PAMPS•$NH_3$ was formed. The PAMPS•$NH_3$ was screen printed onto the electrodes and then heated in a 200° C. oven to form a porous PAMPS•$NH_3$ layer. In this example, the molar ratio between AMPS and $NH_3$ was 10 to 3, and the conductive elements in the porous layer involve hydrogen and ammonium ions. The ammonia molecule can be replaced with other primary, secondary, or tertiary amines, such as trimethylamine, triethylamine, phenylmethylamine, etc. The molar ration of ammonia or amine to AMPS can be between 0 and 1.

EXAMPLE 4

The procedure in Example was similar to that in Example 3, except that 0.66 g of 25% ammonia water was used in the polymerization reaction, representing a 1 to 1 molar ratio between AMPS and $NH_3$. In order to form a porous PAMPS•$NH_3$, the temperature during heat treatment was raised to 230° C., instead of the temperature of 200° C. in Example 3. This indicates that when the ratio of $NH_3$ relative to AMPS is increased, the heat treatment temperature must also be increased.

All the humidity sensors made in Examples 2–4 showed similar response curves as in FIGS. 2 and 3. The nonporous PAMPS film can also be formed over the electrodes using a dipping method. However, the screen printing method, which allows tens of sensing elements to be formed simultaneously, appears to be a more economic approach for mass production.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method for making poly(2-acryl-amido-2-methyl-propane sulphonic acid)-based humidity sensing element comprising the steps of:
   (a) obtaining a substrate which has a pair of conductive electrodes formed thereon;
   (b) forming a poly(2-acryl-amido-2-methyl-propane sulphonic acid) film on said conductive electrodes;
   (c) subjecting said poly(2-acryl-amido-2-methyl-propane sulphonic acid) film to a heat treatment at temperatures between about 170° C. and 240° C.

2. The method for making porous poly(2-acryl-amido-2-methyl-propane sulphonic acid)-based humidity sensing element according to claim 1 wherein said poly(2-acryl-amido-2-methyl-propane sulphonic acid) is prepared by a polymerization reaction in which a polymerization initiator is added into an aqueous solution containing 2-acryl-amido-2-methyl-propane sulphonic acid monomers.

3. The method for making porous poly(2-acryl-amido-2-methyl-propane sulphonic acid)-based humidity sensing element according to claim 2 wherein said polymerization reaction further includes a step of adding a cation into said aqueous solution containing said 2-acryl-amido-2-methyl-propane sulphonic acid monomers.

4. The method for making porous poly(2-acryl-amido-2-methyl-propane sulphonic acid)-based humidity sensing element according to claim 3 wherein said cation is added into said aqueous solution in the form of a salt selected from the group consisting of lithium hydroxide, potassium hydroxide, sodium hydroxide, and tetra-alkyl ammonium hydroxide.

5. The method for making porous poly(2-acryl-amido-2-methyl-propane sulphonic acid)-based humidity sensing element according to claim 3 wherein said cation is added into said aqueous solution in the form of ammonia, or a primary, secondary, or tertiary amine.

6. The method for making porous poly(2-acryl-amido-2-methyl-propane sulphonic acid)-based humidity sensing element according to claim 3 wherein said cation is lithium which is provided at a molar ratio of 1 to 10 between said lithium and said 2-acryl-amido-2-methyl-propane sulphonic acid, and said heat treatment is conducted at a temperature of about 230° C.

7. The method for making porous poly(2-acryl-amido-2-methyl-propane sulphonic acid)-based humidity sensing element according to claim 3 wherein said cation is $NH_4^+$ which is provided at a molar ratio of 3 to 10 between said $NH_4^+$ and said 2-acryl-amnido-2-methyl-propane sulphonic acid, and said heat treatment is conducted at a temperature of about 200° C.

8. The method for making porous poly(2-acryl-amido-2-methyl-propane sulphonic acid)-based humidity sensing element according to claim 3 wherein said cation is $NH_4^+$ which is provided at a molar ratio of 1 to 1 between said $NH_4^+$ and said 2-acryl-amido-2-methyl-propane sulphonic acid, and said heat treatment is conducted at a temperature of about 230° C.

9. A poly(2-acryl-amido-2-methyl-propane sulphonic acid)-based humidity sensing element comprising:
   (a) a non-conductive substrate which has a pair of conductive electrodes formed thereon;
   (b) a poly(2-acryl-amido-2-methyl-propane sulphonic acid) film formed on said conductive electrodes;
   (c) wherein said poly(2-acryl-amido-2-methyl-propane sulphonic acid) film is formed by first forming a poly(2-acryl-amido-2-methyl-propane sulphonic acid) film on said electrodes, then subjecting said poly(2-acryl-amido-2-methyl-propane sulphonic acid) film to a heat treatment at temperatures between about 170° C. and 240° C.

10. The porous poly(2-acryl-amido-2-methyl-propane sulphonic acid)-based humidity sensing element according to claim 9 wherein said non-porous poly(2-acryl-amido-2-methyl-propane sulphonic acid) is prepared by a polymerization reaction in which a polymerization initiator is added into an aqueous solution containing 2-acryl-amido-2-methyl-propane sulphonic acid monomers.

11. The porous poly(2-acryl-amido-2-methyl-propane sulphonic acid)-based humidity sensing element according to claim 9 wherein said polymerization reaction further includes a step of adding a cation into said aqueous solution containing said 2-acryl-amido-2-methyl-propane sulphonic acid monomers, such that said poly(2-acryl-amido-2-methyl-propane sulphonic acid) is represented by the formula of PAMPS•X; wherein AMPS is a 2-acryl-amido-2-methyl-propane sulphonyl group, and X is a cation.

12. The porous poly(2-acryl-amido-2-methyl-propane sulphonic acid)-based humidity sensing element according to claim 11 wherein said cation is selected from the group consisting of hydrogen, lithium, potassium, sodium, ammonium, primary, secondary, and tertiary amine ions, and tetra-alkyl ammonium ions.

13. The porous poly(2-acryl-amido-2-methyl-propane sulphonic acid)-based humidity sensing element according to claim 12 wherein said cation is lithium which is provided at a molar ratio of 1 to 10 between said lithium and said 2-acryl-amido-2-methyl-propane sulphonic acid, and said heat treatment is conducted at a temperature of about 230° C.

14. The porous poly(2-acryl-amido-2-methyl-propane sulphonic acid)-based humidity sensing element according to claim 12 wherein said cation is $NH_4^+$ which is provided at a molar ratio of 3 to 10 between said $NH_4^+$ and said 2-acryl-amido-2-methyl-propane sulphonic acid, and said heat treatment is conducted at a temperature of about 200° C.

15. The porous poly(2-acryl-amido-2-methyl-propane sulphonic acid)-based humidity sensing element according to claim 12 wherein said cation is $NH_4^+$ which is provided at a molar ratio of 1 to 1 between said $NH_4^+$ and said 2-acryl-amnido-2-methyl-propane sulphonic acid, and said heat treatment is conducted at a temperature of about 230° C.

16. The method for making porous poly(2-acryl-amido-2-methyl-propane sulphonic acid)-based humidity sensing element according to claim 1 wherein said heat treatment is conducted at temperatures of between 200° C. and 240° C.

17. The porous poly(2-acryl-amido-2-methyl-propane sulphuric acid)-based humidity sensing element according to claim 1 wherein said heat treatment is conducted at temperatures of between 200° C. and 240° C.

* * * * *